(12) United States Patent
Darcey

(10) Patent No.: US 6,641,549 B2
(45) Date of Patent: Nov. 4, 2003

(54) CUSTOM-MOLDABLE SUPPORT FOR PATELLAR TENDINITIS

(75) Inventor: Thomas D. Darcey, Mooresville, NC (US)

(73) Assignee: BSN Medical, Inc., Wilmington, DE (US)

( * ) Notice: Subject to any disclaimer, the term of this patent is extended or adjusted under 35 U.S.C. 154(b) by 105 days.

(21) Appl. No.: 09/776,988

(22) Filed: Feb. 5, 2001

(65) Prior Publication Data
US 2002/0147421 A1 Oct. 10, 2002

(51) Int. Cl.[7] .................................................. A61F 5/00
(52) U.S. Cl. ................................ 602/8; 602/6; 602/23; 602/26
(58) Field of Search ......................... 602/5, 6, 8, 61, 602/62, 60, 26, 23; 128/882

(56) References Cited

U.S. PATENT DOCUMENTS

| | | | |
|---|---|---|---|
| 4,425,912 A | * 1/1984 | Harper | ............................ 2/24 |
| 4,777,946 A | * 10/1988 | Watanabe et al. | ........... 128/882 |
| 4,872,448 A | * 10/1989 | Johnson, Jr. | ......... 128/DIG. 20 |
| 4,893,355 A | 1/1990 | Ritter | |
| 5,277,697 A | 1/1994 | France et al. | |
| 5,514,083 A | 5/1996 | Smith, III | |
| 5,613,943 A | 3/1997 | Palumbo | |
| 5,755,678 A | * 5/1998 | Parker et al. | ................... 602/6 |
| 5,800,371 A | * 9/1998 | Winn | ........................ 473/207 |
| 5,807,298 A | 9/1998 | Palumbo | |
| 5,947,913 A | 9/1999 | Palumbo | |
| 5,980,474 A | * 11/1999 | Darcey | ........................... 602/5 |
| 6,080,124 A | * 6/2000 | Falk et al. | ..................... 602/23 |
| 6,152,892 A | * 11/2000 | Masini | .......................... 602/6 |
| 6,231,533 B1 | * 5/2001 | Novich et al. | ................. 602/7 |

* cited by examiner

*Primary Examiner*—Danton D. DeMille
*Assistant Examiner*—Q. Thanh
(74) *Attorney, Agent, or Firm*—Adams Evans P.A.

(57) ABSTRACT

A knee pad assembly for relieving the symptoms of patellar tendinitis, including a pad adapted for being positioned against and molded onto a lower leg in the region of the knee for lying in closely-conforming relation against and applying radially-directed pressure to the attachment site of the patellar tendon to the patella, to the knee joint, and to at least one epicondyle of the tibia. The pad is hardened into a rigid structure for therapeutic use and includes an initially flexible inner substrate impregnated or coated with a reactive system. The system remains stable when maintained in substantially moisture-free conditions and hardens upon exposure to moisture to form a rigid, self-supporting structure having a shape conforming to the lower leg to which the pad is molded during curing. A flexible cover encloses the substrate, and cooperates with the pad for maintaining the pad in its closely-conforming position against the lower leg.

30 Claims, 13 Drawing Sheets

CUSTOM-MOLDABLE SUPPORT FOR PATELLAR TENDINITIS

TECHNICAL FIELD AND BACKGROUND OF THE INVENTION

This invention relates to a custom-molded pad for relief of the symptoms of patellar tendinitis. Patellar tendinitis is the inflamation of the patellar tendon at the point at which it attaches to either the inferior pole of the patella or the tibial tuberosity, or the inflamation of the quadriceps tendon at the point at which it attaches to the superior pole of the patella. Patellar tendinitis is primarily caused by continued stress on the patellar or quadriceps tendons. Although repetitive jumping, such as that which occurs while playing volleyball, is an activity commonly associated with aggravating the onset of patellar tendinitis, there are several other activities that can cause the condition, such as running, walking or bicycling. As discussed below, each of these activities involves repetitive use of the same muscle groups and tendons in the legs, which often leads to the inflammation and tearing of the tendons associated with patellar tendinitis.

Standard treatment for a typical case of patellar tendinitis involves resting and applying ice to the affected knee. Non-steroidal anti-inflammatory drugs may also be prescribed to alleviate swelling and pain in the affected area. In many cases, an external device will also be prescribed for use by the patient to support the affected muscles and tendons during normal activities. Such devices help reduce the risk of further injury to the knee. Although it is rare, some severe or chronic cases of patellar tendinitis require arthroscopic or open surgical treatment for tendon decompression or tenodesis.

Prior art methods available for treating patellar tendinitis often fail to provide adequate pain relief. A typical elastic strap used to treat patellar tendinitis extends around the lower leg beneath the knee and seeks to provide concentrated support directly over the patellar tendon. While such devices may provide some degree of generalized support to the injured area, they have limited effectiveness because they provide such support in a manner that inhibits adequate blood flow to the lower limb, and fails to direct concentrated support to the injured area. Any palliative benefits which are actually achieved are quickly offset by the increased pain and numbness in the lower leg caused by pulling the strap too tightly around the leg in an attempt to achieve some degree of support from the device. Those straps which do provide additional padding over the inflamed area are likewise inadequate because the padding is typically so thick that the strap will not conform to the shape of the lower leg without applying an increased amount of pressure over the injured area. This increased pressure causes the padding to compress against the lower leg, and can compromise circulation in the same manner as seen with unpadded straps. Such padded and unpadded elastic straps not only fail to provide concentrated support directly over the injured area, but also fail to provide a secure, custom fit which addresses the unique anatomical needs of the individual wearer.

The knee pad assembly of the present invention is inexpensive to produce, easy to fabricate, comfortable to wear, and offers an improved alternative to conventional elastic bands and other standard treatments for patellar tendinitis. The assembly includes a custom-fitted pad which is molded to conform to the exact shape of the anatomy of a wearer. The pad is first placed against the wearer's lower leg and cured to a custom-fitted shape. The pad is then secured over or adjacent the inflamed area of the lower leg using an adjustable elastic strap. The strap and the pad cooperate together to provide a custom-fitted device that produces concentrated, radially directed support to the injured tendon without compromising blood circulation to the lower leg. Unlike some prior art knee bands which resort to thick layers of padding in an attempt to provide support, the pad used in the knee pad assembly of the present invention provides adequate support to the injured area by using thin layers of rigid, resin-impregnated fabric. This results in a thin, lightweight pad against which a reduced amount of radially-directed pressure needs to be applied to achieve a higher degree of support to the knee. This promotes blood flow to the injured area and to the lower leg, while accelerating the healing process.

The knee pad assembly of the present invention uses a moisture curable resin system to quickly and easily mold the pad to the shape of the lower leg. Upon curing, the moisture curable resin system yields a very rigid pad having a custom-fitted shape that conforms to the area of the lower leg to which the pad was initially molded. No heat is required to activate curing of the resin. A source of water is the only additional material necessary to achieve a cure. While atmospheric moisture alone will cure the knee pad into its hardened position in a relatively shortened period of time, the resin in or on the pad will typically be activated by immersing the pad in water prior to fitting the pad to an individual's lower leg. Once a final cure is achieved, the knee pad will maintain its custom-fitted shape regardless of whether the pad is subsequently exposed to heat or moisture.

SUMMARY OF THE INVENTION

Therefore, it is an object of the invention to provide a custom-molded knee pad assembly which is easy to fabricate.

It is another object of the invention to provide a knee pad assembly which provides concentrated, radially-directed support to the knee area without compromising circulation of blood to the injured area and to the lower leg.

It is another object of the invention to provide a knee pad assembly that hardens in the presence of moisture to form a very rigid yet very lightweight protective pad.

It is another object of the invention to provide a knee pad assembly that can be quickly and easily positioned on and removed from a wearer's forearm by the wearer.

It is another object of the invention to provide a knee pad assembly that is stored in a moisture-proof pouch until ready for application to the muscles and tendons to be supported.

These and other objects of the invention are achieved in the preferred embodiments disclosed below by providing a knee pad assembly for relieving the symptoms of patellar tendinitis. The knee pad assembly includes a pad adapted for being positioned against and molded onto a lower leg in the region of the knee for lying in closely-conforming relation against and applying radially-directed pressure to the attachment site of the patellar tendon to the patella, to the knee joint, and to at least one epicondyle of the tibia. The pad is hardened into a rigid structure for therapeutic use, and includes an initially flexible inner substrate impregnated or coated with a reactive system. The system remains stable when maintained in substantially moisture-free conditions and hardens upon exposure to moisture to form a rigid, self-supporting structure having a shape conforming to the lower leg to which the pad is molded during curing. A flexible cover encloses the substrate, and a support cooperates with the pad for maintaining the pad in its closely-conforming position against the lower leg.

According to one preferred embodiment of the invention, the support includes an elongate strap having an outer surface and first and second ends. The first end of the strap is releasably attached to an upper surface of the pad, thereby permitting the strap to extend around the lower leg for securing the pad in the closely conforming configuration against the lower leg.

According to another preferred embodiment of the invention, the inner layer includes a plurality of overlaid thicknesses of fiberglass.

According to yet another preferred embodiment of the invention, the plurality of thicknesses includes at least three and no more than five layers.

According to yet another preferred embodiment of the invention, the outer layer includes an innermost foam layer overlying at least one side of the substrate.

According to yet another preferred embodiment of the invention, the outer layer includes an innermost foam layer enclosing the substrate therein.

According to yet another preferred embodiment of the invention, the foam layer is selected from the group consisting of closed-cell ethylene vinyl acetate and polyurethane.

According to yet another preferred embodiment of the invention, the outer layer further includes a flexible protective cover enclosing the foam layer, wherein the substrate, foam layer and cover are joined together to form a unitary structure for being molded while flexible to an aspect of the lower leg.

According to yet another preferred embodiment of the invention, the cover is formed of a polyester sheeting fabric.

According to yet another preferred embodiment of the invention, the length of the pad is at least twice as great as the width of the pad.

According to yet another preferred embodiment of the invention, the reactive system includes a blended polyisocyanate, polyol, catalyst and stabilizer.

According to yet another preferred embodiment of the invention, the knee pad assembly includes a loop attached to the upper surface and adapted for receiving the strap therethrough for securing the pad against the lower leg.

According to yet another preferred embodiment of the invention, the knee pad assembly includes a first fastener attached to the upper surface for cooperating with a complementary second fastener attached to the strap for holding the pad in place on the lower leg while being worn.

According to yet another preferred embodiment of the invention, one of the first and second fasteners is a patch of looped material, and the other of the first and second fasteners is a complementary patch of hooked material.

According to yet another preferred embodiment of the invention, the first end of the strap includes a fastening ring connected thereto and adapted for receiving said second end therethrough for securing the strap around the lower leg.

According to yet another preferred embodiment of the invention, the knee pad assembly includes a third fastener attached to the second end of the strap for being releasably connected to the outer surface, thereby permitting the strap to be secured around the lower leg.

According to yet another preferred embodiment of the invention, the outer surface of the strap is hook-and-loop material.

According to yet another preferred embodiment of the invention, the third fastener is a patch of hook-and-loop material complementary to the outer surface.

According to yet another preferred embodiment of the invention, a knee pad assembly product for relieving the symptoms of patellartendinitis is provided which includes an outer pouch formed of a moisture-impervious material. A pad is positioned in the pouch in substantially moisture-free conditions and sealed therein against entry of moisture until use. The pad is adapted for being positioned against and molded onto a lower leg in the region of the knee for lying in closely-conforming relation against and applying radially-directed pressure to the attachment site of the patellar tendon to the patella, to the knee joint and to at least one epicondyle of the tibia and hardened into a rigid structure for therapeutic use. The pad includes an initially flexible substrate impregnated or coated with a reactive system. The system remains stable when maintained in substantially moisture-free conditions and hardens upon exposure to moisture to form a rigid, self-supporting structure having a shape conforming to the lower leg to which the pad is molded during curing. A flexible outer layer encloses the substrate, and a support cooperates with the pad for maintaining the pad in its closely-conforming position against the lower leg.

BRIEF DESCRIPTION OF THE DRAWINGS

Some of the objects of the invention have been set forth above. Other objects and advantages of the invention will appear as the invention proceeds when taken in conjunction with the following drawings, in which.

DESCRIPTION OF THE PREFERRED EMBODIMENT AND BEST MODE

Figure 1:
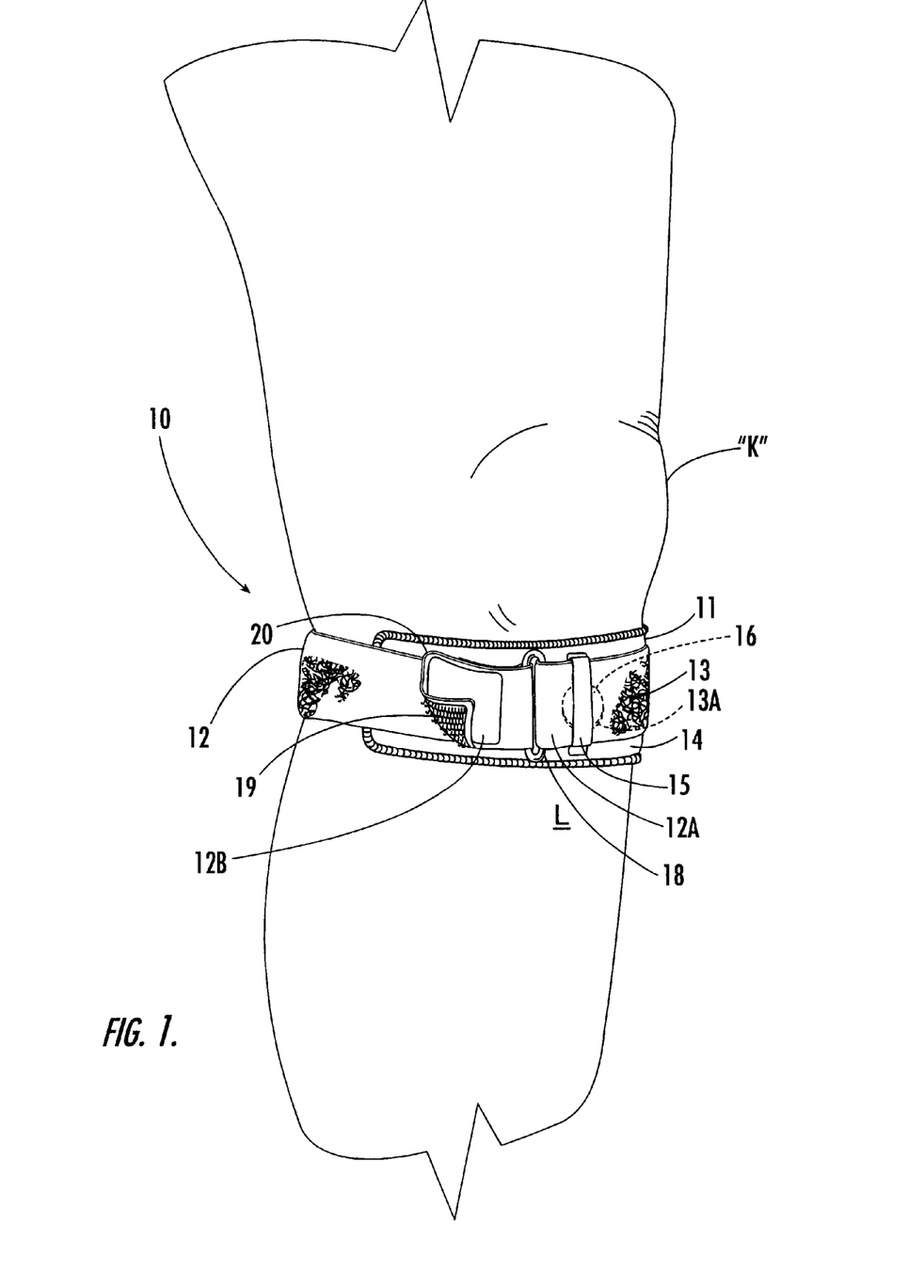
FIG. 1 is an environmental perspective view of a knee pad assembly according to one embodiment of the invention showing one manner in which the knee pad is releasably secured around a lower leg.

Referring now specifically to the drawings, a knee pad assembly is illustrated in FIG. 1 and shown generally at reference numeral 10. The assembly 10 includes a pad 11 which, as is described more fully in reference to FIGS. 7, 8 and 9 below, is custom-molded to fit immediately below a wearer's knee "K", and is held in place by an elongate strap 12. Although the strap 12 may be formed from any suitable flexible substance, the strap 12 is preferably formed of a narrow length of elasticized woven or knitted material having a raised, fibrous surface 13 to which a patch of looped material 13 A is attached. The pad 11 has an upper surface 14 to which the ends of a relatively narrow strap loop 15 are sewn. The loop 15 extends across the width of the pad 11 and maintains the pad 11 in place against the lower leg "L". A second patch of hooked material 16 is attached to the upper surface 14 of the pad 11. The strap 12 has a first end 12A to which a D-ring 18 is secured. A third patch of hooked material 19 is sewn, glued or otherwise attached to a second end 12B of the strap 12. The assembly 10 is positioned on the lower leg by first passing the strap 12 through the D-ring 18 so that the strap 12 extends around the circumference of the lower leg "L". The pad 11 is then secured against the lower leg "L" by pulling the end 12B of the strap 12 so the pad 11 fits closely against the lower leg "L", and securing the third patch of hooked material 19 to the fibrous surface 13 at the desired position to maintain the pad 11 in the desired position against the lower leg "L". The first end 12A of the strap 12 is removably secured to the to the pad 11 by securing the second patch of hooked material 16 to the patch of looped material 13A, or alternatively, by securing the second patch of hooked material 16 directly to the fibrous surface 13.

Figure 2:
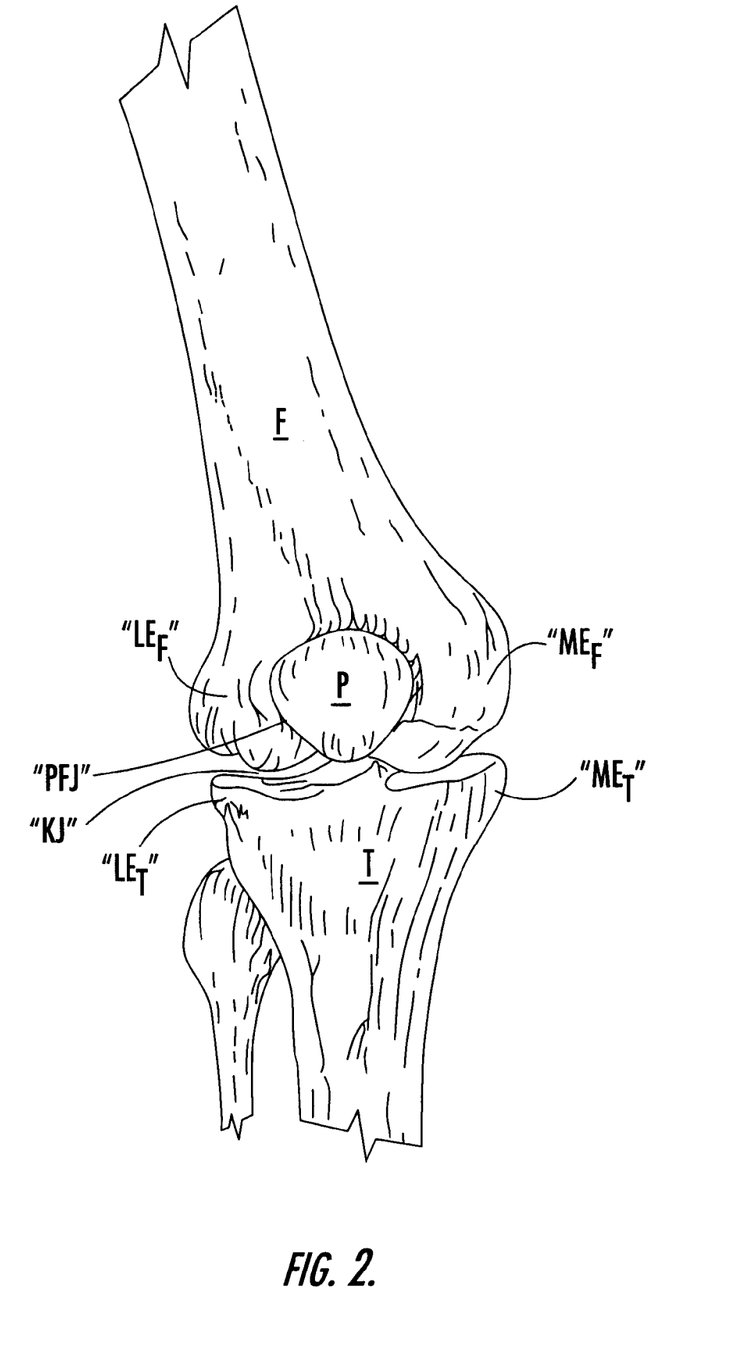
FIG. 2 is a perspective view of the bones and joints of the right knee of a human.
Figure 3A:
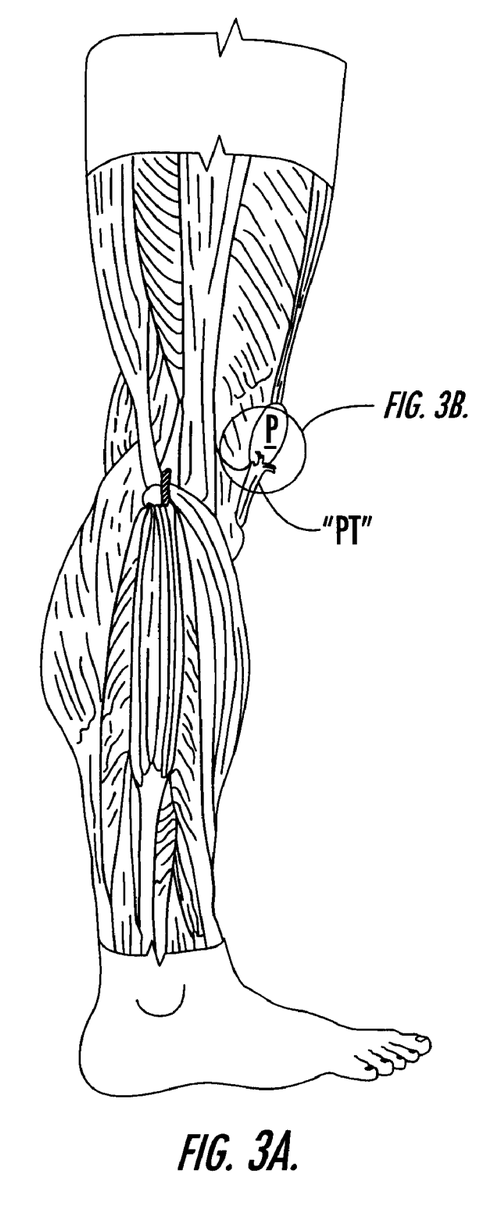
FIG. 3A is a cut-away perspective view of the right leg of a human showing the muscles and tendons connected to the patella and affected by a form of patellar tendinitis known as "jumper's knee"
Figure 3B:
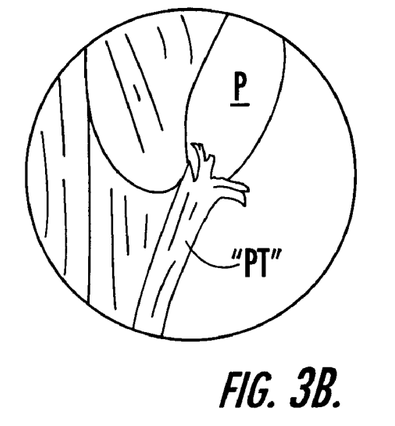
FIG. 3B is a cut-away perspective view of the inferior patellar region of the leg shown in FIG. 3A illustrating the inflamed and torn patellar tendon affected by jumper's knee.

Referring now to FIGS. 2, 3A and 3B, the anatomy affected by patellar tendinitis is shown. FIG. 2 shows the underlying bone and joint structure of the knee of a right leg of a human. The knee is generally located at the junction of the patella "P" with the lateral epicondyle "$LE_F$" and medial epicondyle "$ME_F$" of the femur "F", and with the lateral epicondyle "$LE_T$" and the medial epicondyle "$ME_T$" of the tibia "T". The patella "P" articulates with the patellofemoral joint or groove "PFJ", which lies between the lateral and medial epicondyles "$LE_F$" and "$ME_F$" of the femur "F". The point at which the patella "P" and the lateral and medial epicondyles "$LE_F$" and "$ME_F$" of the femur "F" meet the lateral and medial epicondyles "$LE_T$" and "$ME_T$" of the tibia "T" forms the knee joint "KJ".

Figure 4A:
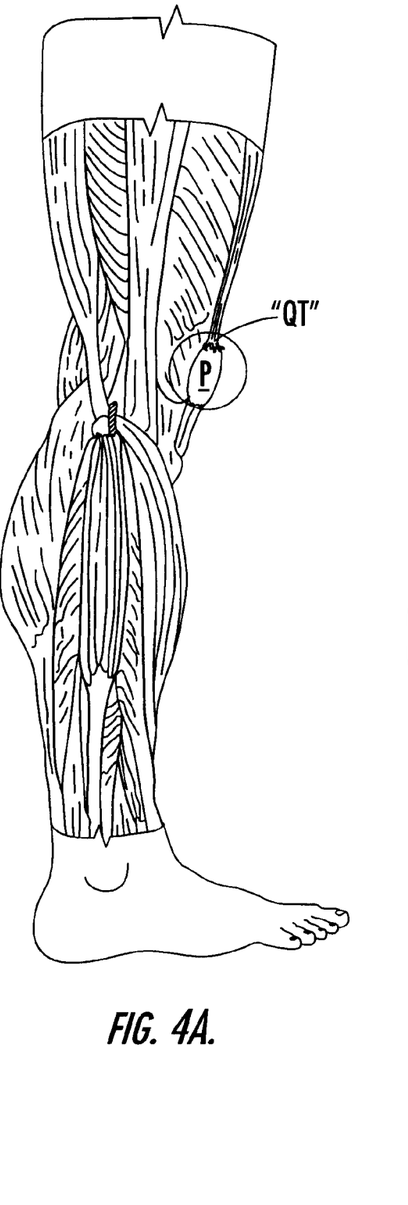
FIG. 4A is a cut-away perspective view of the right leg of a human showing the muscles and tendons connected to the patella and affected by a form of patellar tendinitis which results from damage to the quadriceps tendon.
Figure 4B:
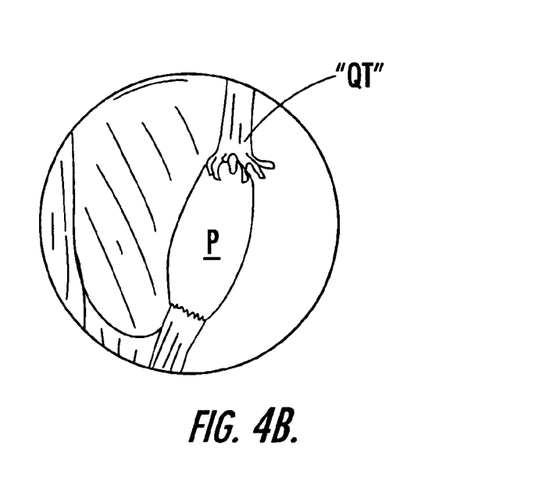
FIG. 4B is a cut-away perspective view of the superior patellar region of the leg shown in FIG. 4A illustrating the inflamed and torn quadriceps tendon.
Figure 5:
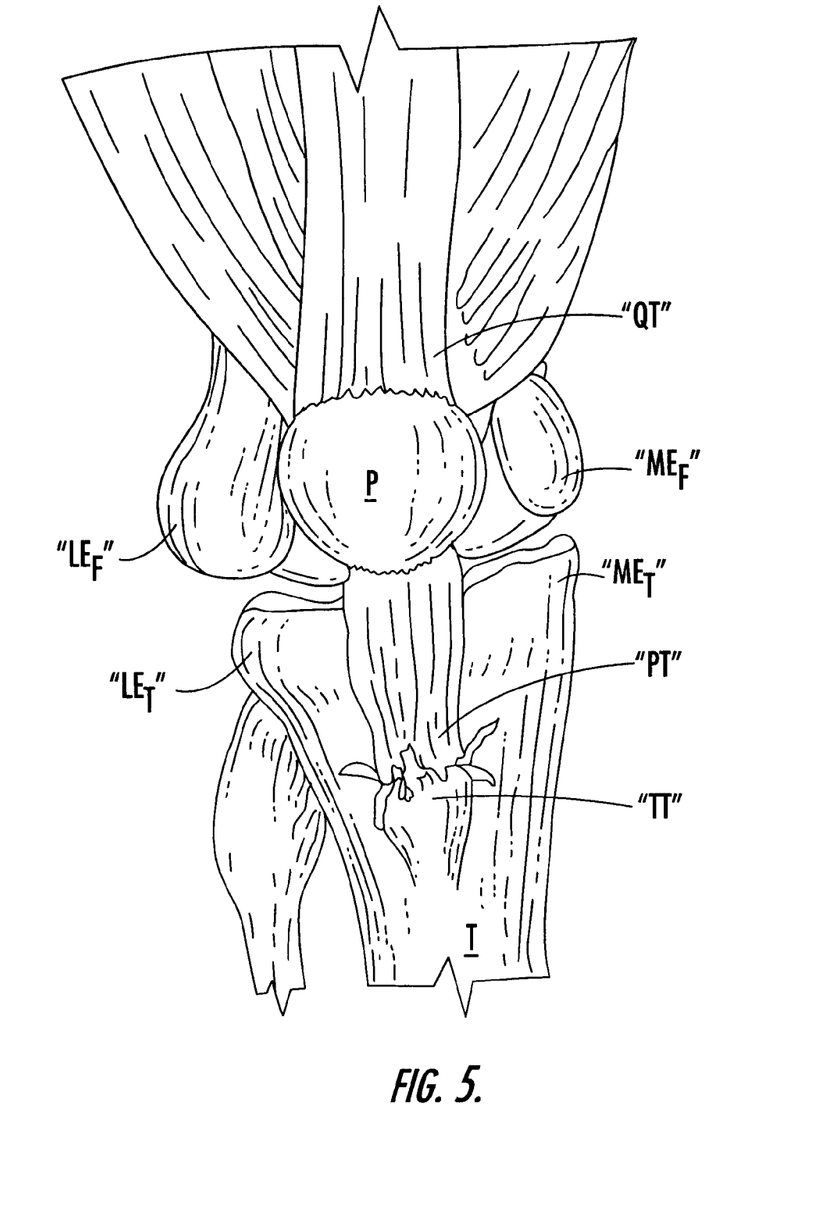
FIG. 5 is a cut-away perspective view of the right knee of a human leg illustrating an inflamed and torn patellar tendon affected by Osgood-Schlatter's disease.

As is shown in FIGS. 3A and 3B, one common form of patellar tendinitis known as "jumper's knee" occurs as a result of degeneration and tearing of the patellar tendon "PT" along its point of attachment to the inferior pole of the patella "P". FIGS. 4A and 4B show another form of patellar tendinitis which is caused by degeneration and tearing of the quadriceps tendon "QT" at its point of attachment to the superior pole of the patella "P". A third form of patellar tendinitis known as Osgood-Schlatter's disease is shown in FIG. 5. Osgood-Schlatter's disease commonly occurs in adolescents and is caused by the degeneration and tearing of the patellar tendon "PT" at the point where the patellar tendon "PT" attaches to the tibial tuberosity "TT".

Throughout this specification, the knee pad assembly 10 is described and shown for use in relieving the symptoms of jumper's knee. However, the knee pad assembly 10 may alternatively be custom-fitted along any part of the upper or lower leg near the knee to provide relief from any one of the forms of patellar tendinitis discussed above and shown in FIGS. 3A–5.

Figure 6:
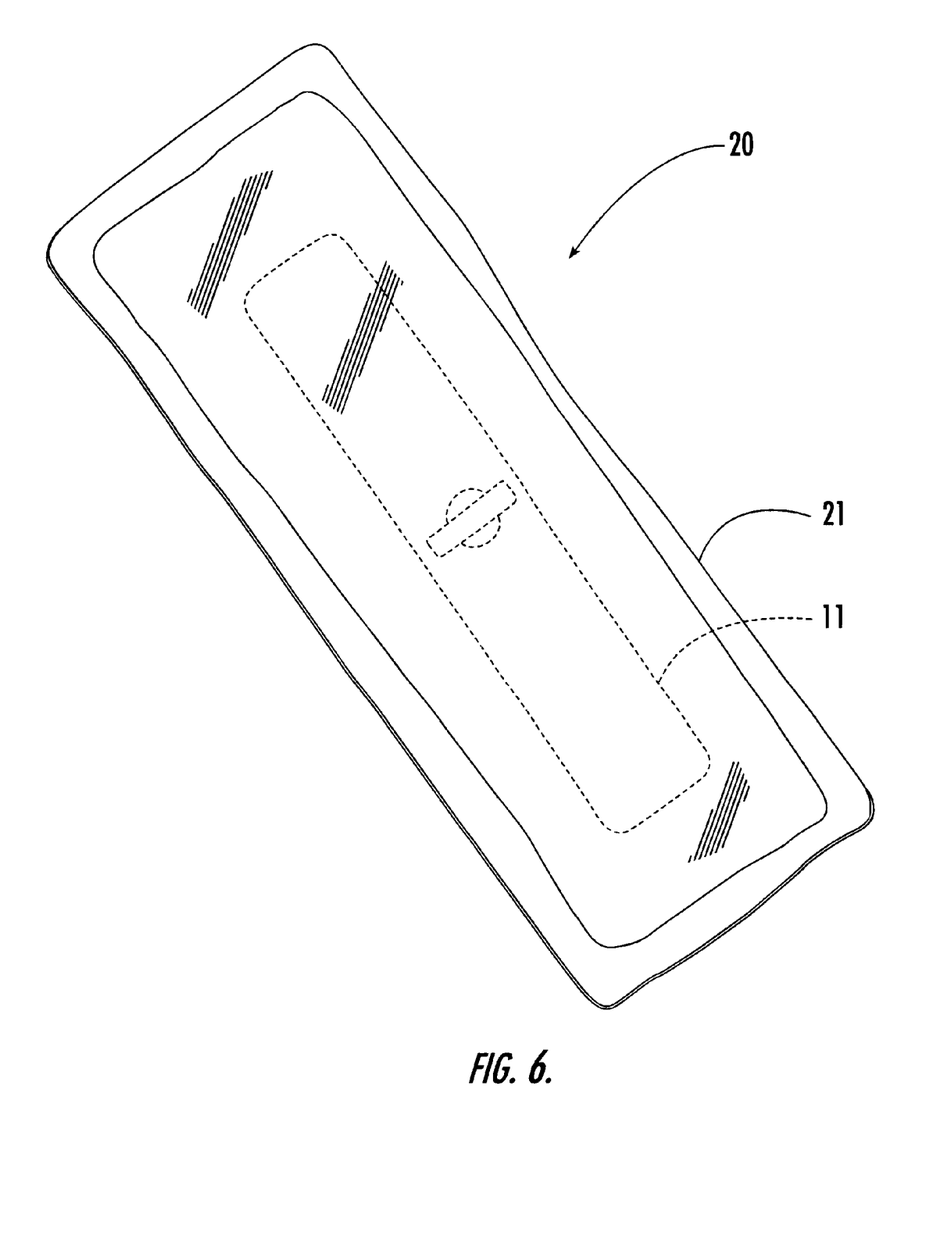
FIG. 6 is a perspective view of a knee pad assembly product according to one embodiment of the invention.

Referring now to FIG. 6, a knee pad product according to one embodiment of the invention is illustrated and shown generally at reference numeral 20. The knee pad product includes an outer moisture-impervious foil and laminated pouch 21, in which a pad 11 is sealed in the absence of moisture. The pouch 21 is preferably formed from a 0.5 mil aluminum foil sheet sandwiched between two layers of low density polyethylene film. Each layer of film preferably has a thickness of 2 mils. The pouch 21 may also include an outermost layer of laminated 60 gauge, biaxially oriented nylon film. When the pouch 21 is properly sealed, this laminate structure will prevent moisture from entering the pouch indefinitely.

Figure 7:
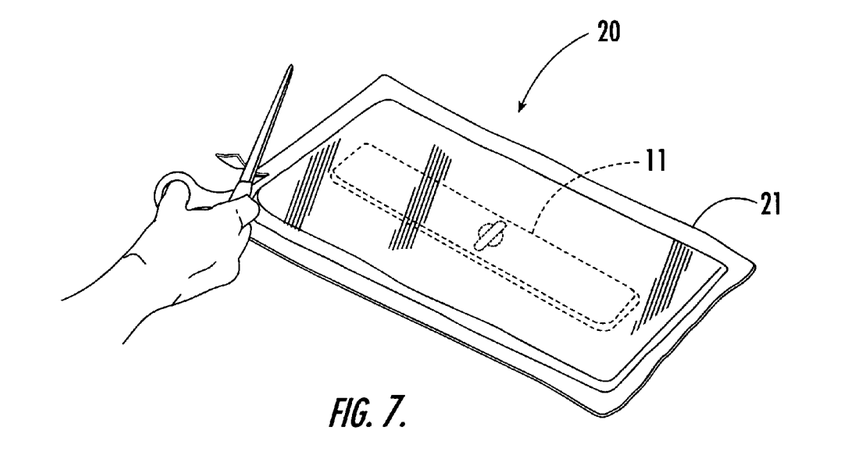
FIG. 7 is a perspective view of the knee pad assembly product shown in FIG. 6 showing the knee pad being removed from a moisture-impervious pouch by opening the pouch immediately prior to initiating the curing and custom-fitting process.
Figure 8:
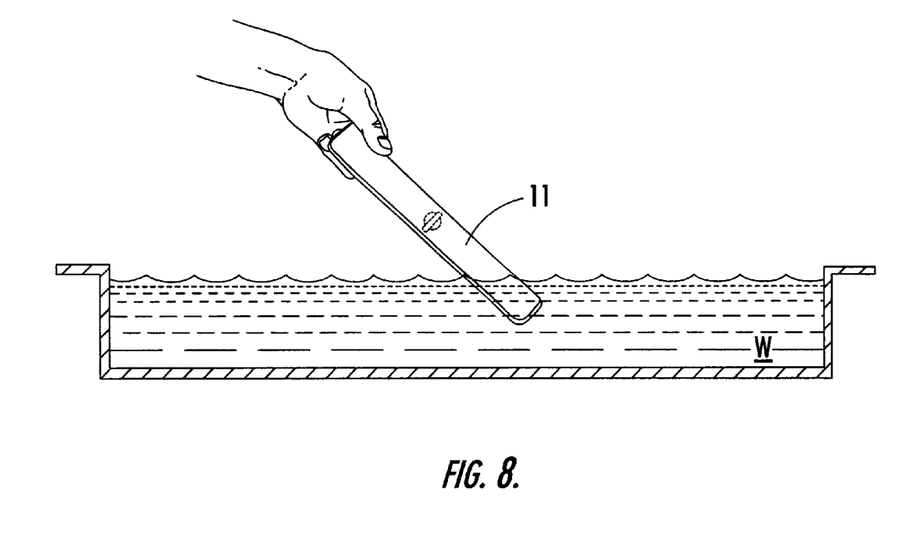
FIG. 8 illustrates activation of the moisture-curable resin in the knee pad.

Referring now to FIG. 7, the moisture-impervious pouch may be opened with scissors, a knife or another sharp object so that the pad 11 can be removed from the pouch 21. As is shown in FIG. 8, after being removed from the pouch 21, the pad 11 is immersed in water "W" to activate the curing process. The curing process may alternatively be activated by spraying the pad 11 with water.

Figure 9:
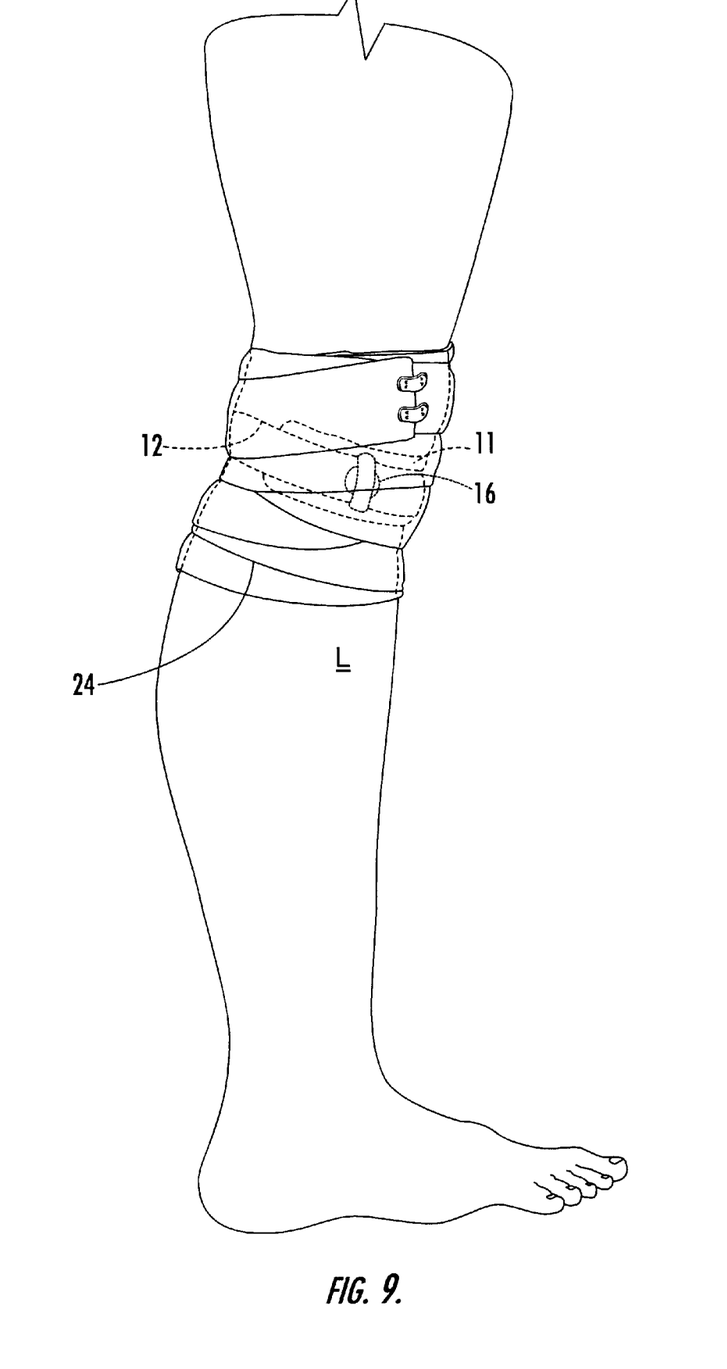
FIG. 9 is an environmental perspective view showing the knee pad assembly being custom-fitted to the knee of a wearer.

Referring now to FIG. 9, after the pad 11 has been immersed in water, it is positioned on the lower leg "L" over the inflamed area. The strap 12 is then attached to the first patch of hooked material 16 and is wrapped around the lower leg "L" and loosened or tightened as needed to ensure a correct fit. An elastic bandage 24 is then wrapped around the lower leg "L" to completely cover the strap 12 and pad 11. The bandage 24 is left in place in this position for a period of time sufficient to allow the resin in or on the pad 11 to harden and form the pad 11 into the desired confirmation against the lower leg "L". The individual to which the pad 11 is being fitted must be advised not to attempt to flex or extend the knee during the curing process to ensure that an accurate custom fit is achieved.

Figure 10:
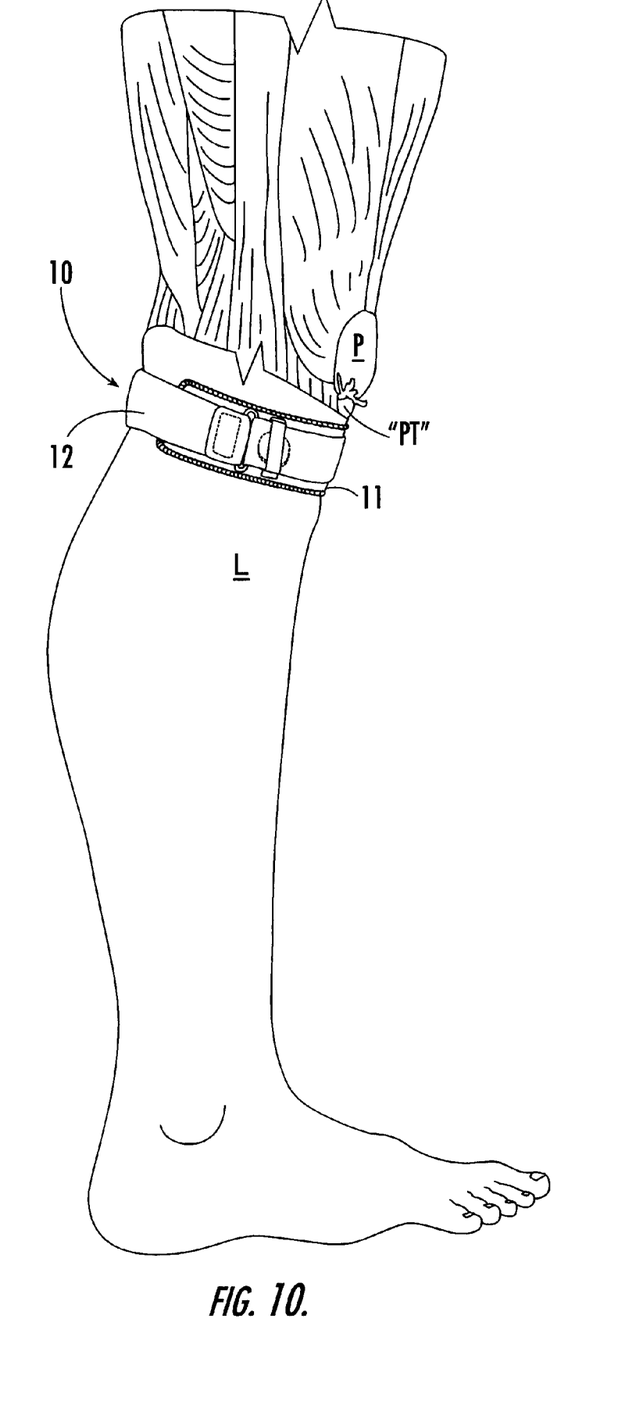
FIG. 10 is a cut-away environmental perspective view showing the knee pad assembly in use after the curing process has been completed.

After the curing process is completed, the bandage 24 is removed. FIG. 10 shows the fully cured knee pad assembly 10 positioned around the lower leg "L", with the custom-fitted pad 11 cooperating with the strap 12 to exert radially-directed pressure against the muscles and injured patellar tendon "PT" to provide relieve from the pain associated with patellar tendinitis.

Figure 11:
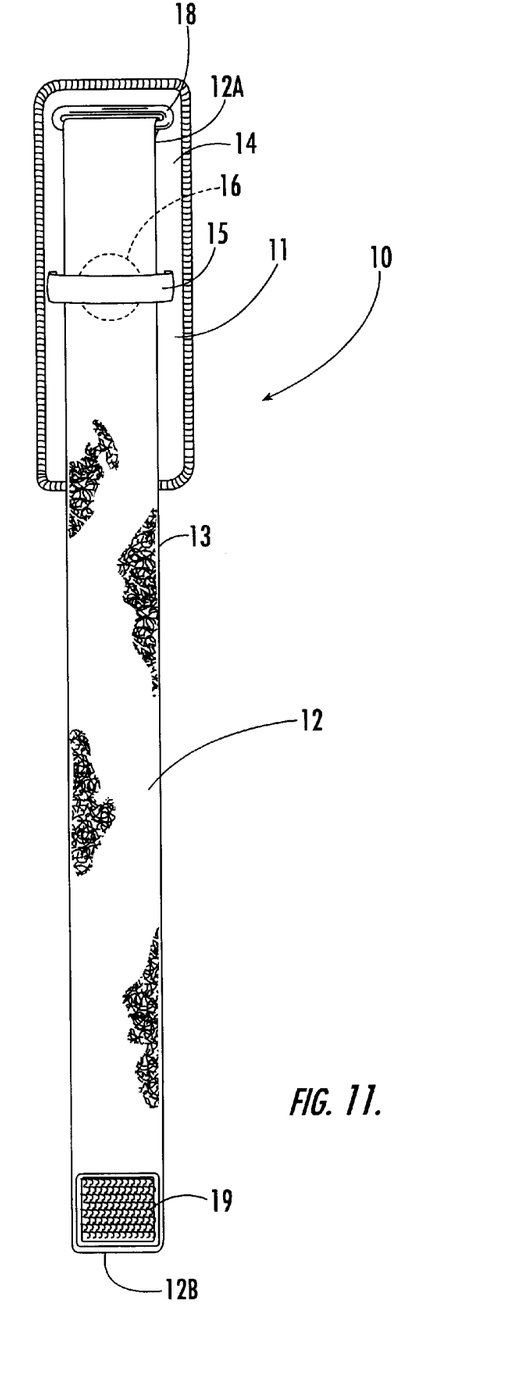
FIG. 11 is a top plan view of the knee pad assembly.
Figure 12:
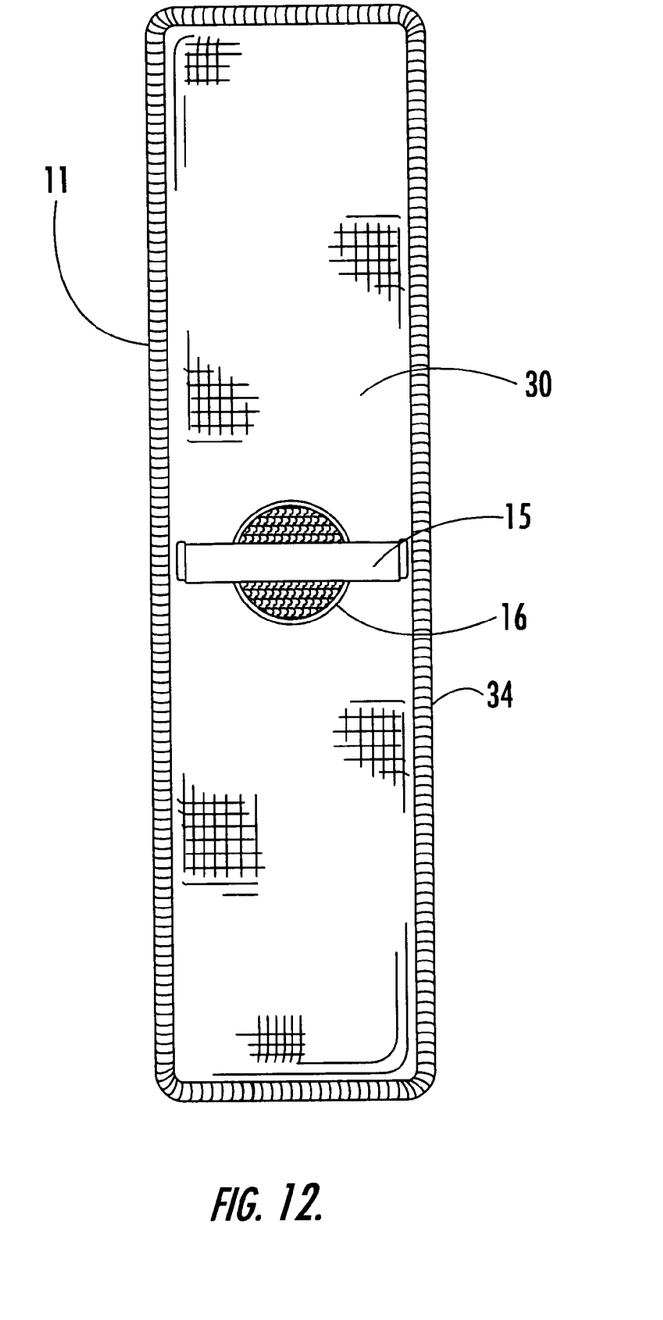
FIG. 12 is a top plan view of the knee pad used in the knee pad assembly shown in FIG. 11.

Referring now to FIG. 11, a fully-assembled knee pad assembly 10 is shown prior to being custom-fitted to a wearer's leg. The strap 12 is releasably connected to the pad 11 using the first patch of hooked material 16, which is attached to the center of the pad 11 and cooperates with the fibrous surface 13. FIG. 12 shows the pad 11 prior to being custom-fitted around the lower leg and with the strap 12 removed. The pad 11 includes an outer layer 30 which is formed from a flexible fabric casing to which the loop 15 is sewn. Although any suitable fabric may be used, the outer layer 30 is preferably formed from polyester sheeting.

Figure 13:
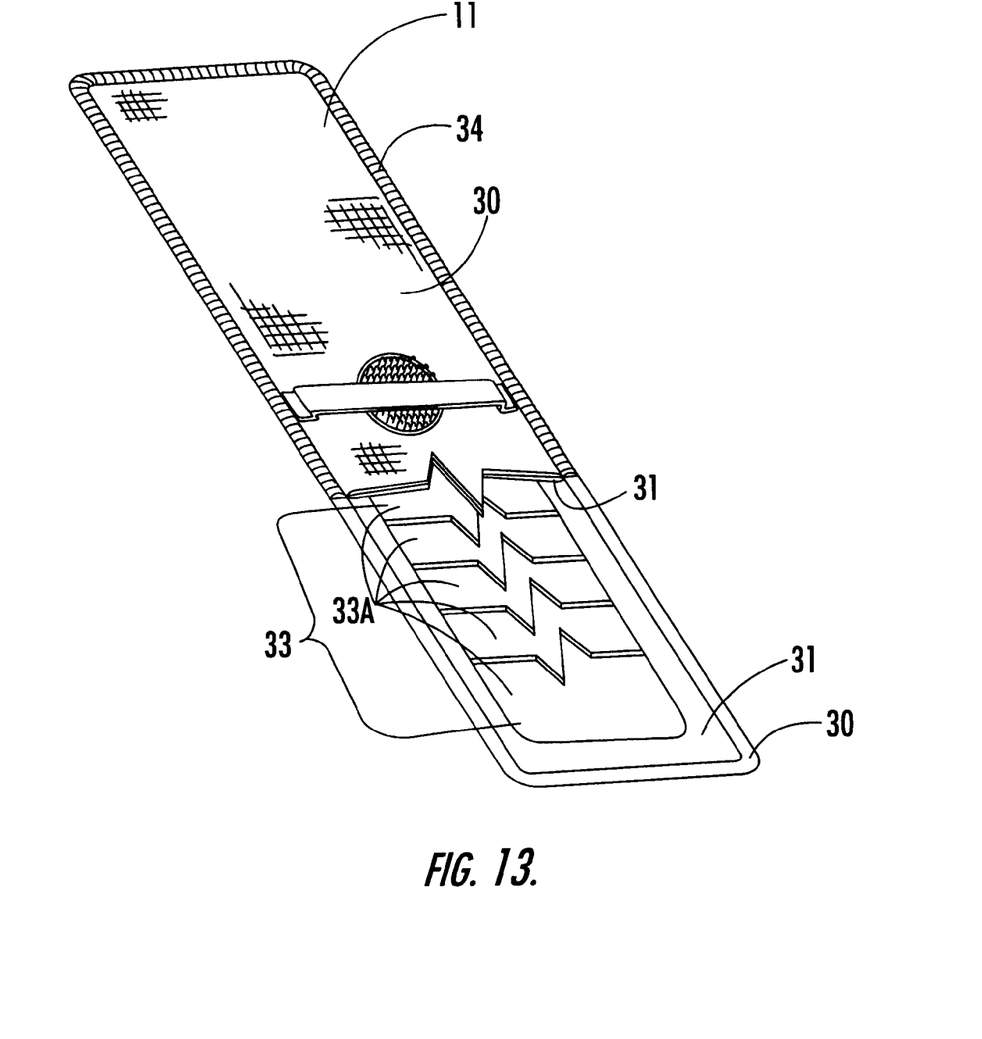
FIG. 13 is a cut-away perspective view of the knee pad shown in FIG. 10 showing the layers of substrate and other materials from which the pad is fabricated.

Referring now to FIG. 13, a flexible cushion layer 31 is provided for being placed closest to the lower leg "L".

Figure 14:
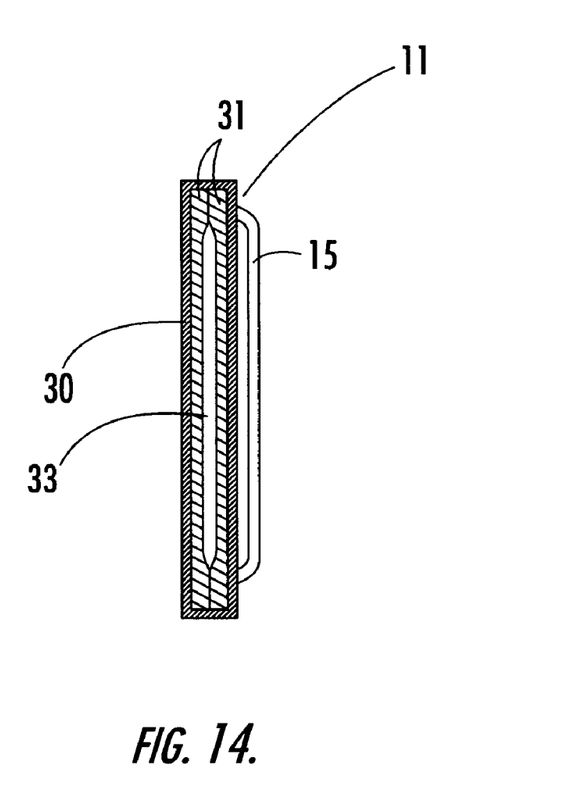
FIG. 14 is a cross-sectional side view of the knee pad showing the substrate layers and other materials of the pad bonded together.

Cushion layer 31 is preferably a laminated, four pound ethylene vinyl acetate ("EVA") micro-perf closed cell foam having a thickness of 1/8 inch. The cushion layer 31 provides a padded, comfortable surface next to the skin, with the EVA being flexible enough to bend easily with the other components of the pad 11 to permit the pad 11 to conform to the shape of the lower leg "L" during the curing process. An initially flexible inner layer 33 is positioned within the cushion layer 31. The inner layer 33 is preferably formed from fiberglass fabric layers 33A, each of which is impregnated with a moisture-curable resin that hardens upon curing to form a rigid structure which retains the shape of the muscles and tendons of the lower leg onto which the pad 11 has been molded. Although any suitable number of fabric layers 33A may be used, the inner layer 33 preferably includes three to five fabric layers 33A. The embodiment of the invention shown in FIG. 13 includes five fabric layers 33A. FIG. 14 shows the inner layer 33 sandwiched between the cushion layer 31 and the outer layer 30 after the pad 11 has been assembled.

Referring again to FIG. 13, the fabric outer layer 30 and the cushion layer 31 are joined around the perimeter by overedge sewing stitches 34. Although the outer fabric layer 30 and cushion layer 31 may be sewn together using an overedge or serging seam, because the outer layer 30 and cushion layer 31 have thermoplastic properties, the outer layer 30 and cushion layer 30 may alternatively be bonded together around the edge using radio-frequency ("RF") welding. RF welding is a particularly efficient method of bonding because it permits tight corners and angles to be formed in the pad 11, some of which cannot be formed using conventional sewing techniques. The inner layer 33 may alternatively be enclosed between the cover 12 and pad 11 using ultrasonic sealing or other suitable adhesives.

Each fiberglass fabric layer 33A is impregnated or coated with a moisture-curable resin such as polyisocyanate. This resin is described in full in the present Applicant's U.S. Pat. No. 4,770,299. The resin is synthesized using a reactive system that remains stable when maintained in substantially moisture-free conditions, yet hardens upon exposure to sufficient moisture to form a rigid, self-supporting structure. A typical formation of the reactive system is as follows:

| Typical Formulation | | |
|---|---|---|
| Isonate ↓ 143L or Mondur ↓ CD or Rubinate ↓ Xl168 | polyisocyanate | 50.0% |
| Pluracol ↓ P1010 | polyol | 46.6% |
| DC-200 Silicone | defoaming agent | 0.30% |
| Benzoyl Chloride | stabilizer | 0.10% |
| Thancat ↓ DM-70 | catalyst | 3.0% |
| | | 100% |

The polyisocyanate resin remains in a viscous state as long as the resin is not exposed to moisture. This permits the substrate to remain flexible and moldable so long as the resin is not exposed to moisture, and for a short period of time after such exposure occurs. The rate at which the resin cures can be controlled to some extent by the quantity of water to which the resin is exposed. Briefly immersing the resin in water will cause the resin to rapidly cure. In contrast, merely exposing the resin to open air will result in a curing process having a significantly slower reaction rate which will be proportional to the amount of moisture in the air to which the resin is exposed.

The individual fiberglass fabric layers 33A are preferably die-cut to shape. In addition, while each fabric layer 33A preferably has the same width, a different width may be used for each layer 33A. The degree of overlap and non-overlap resulting from the varying widths provides a variable thickness across the pad 11 after curing, with a relatively thick predetermined area where increased rigidity is desired and a relatively thin area where increased flexibility is desired. The manner of varying the widths of the fabric layers 33A is described in detail in Applicant's prior U.S. Pat. No. 5,755, 678.

Although the fabric layers 33A are preferably formed from fiberglass, the inner layer 33 may alternately be formed from a fabric woven or knitted from polypropylene yarns. Such fabric is somewhat more flexible than fiberglass fabric after hardening, and offers some cost savings during production of the knee pad assembly 10. One preferred embodiment of the knee pad assembly 10 has the following specifications:

| | |
|---|---|
| Length of pad 11 | 1.5"–2 inches |
| Width of pad 11 | 1"–1.5 inches |
| Length of loop 15 | 1.25 inches seam-to-seam |
| Diameter of patch of hooked material 16 | .5 inch |
| Width of strap 12 | 1 inch |
| Length of strap 12 | 18"–20 inches |
| Outer layer 30 | Polyester sheeting |
| Cushion layer 32 | .25 inch microperf EVA closed cell foam |
| Number of fiberglass layers 33A | 5 |
| Bandage 24 | 2 inch × 5 yard stretch elastic-free elastic bandage |

A knee pad assembly is described above. Various details of the invention may be changed without departing from its scope. Furthermore, the foregoing description of the preferred embodiment of the invention and the best mode for practicing the invention are provided for the purpose of illustration only and not for the purpose of limitation—the invention being defined by the claims.

I claim:

1. A knee pad assembly for relieving the symptoms of patellar tendinitis, comprising:
    (a) a pad having an upper surface adapted for being positioned against and molded onto a lower leg in the region of the knee for lying in closely-conforming relation against and applying radially-directed pressure to the attachment site of the patellar tendon to the patella, to the knee joint, and to at least one epicondyle of the tibia and hardened into a rigid structure for therapeutic use, said pad comprising:
        (i) an initially flexible inner substrate impregnated or coated with a reactive system, said system remaining stable when maintained in substantially moisture-free conditions and hardening upon exposure to moisture to form a rigid, self-supporting structure having a shape conforming to the lower leg to which the pad is molded during curing;
        (ii) an inner foam layer overlying at least one side of said substrate; and (iii) a flexible cover overlying both sides of said substrate and inner foam layer combined; and
        (iv) a loop comprising a strip having first and second ends which are attached to said upper surface and
    (b) an elongate strap having an outer surface and first and second ends, said strap being disposed through said loop whereby said loop retains said loop restrains said strap against said upper surface of said pad so that the strap may extend around the lower leg for securing the pad in the closely conforming configuration against the lower leg.

2. A knee pad assembly according to claim 1, wherein said inner substrate comprises a plurality of overlaid thicknesses of fiberglass.

3. A knee pad assembly according to claim 2, wherein said plurality of thicknesses comprises at least three and no more than five layers.

4. A knee pad assembly according to claim 2, wherein the inner foam layer encloses the substrate therein.

5. A knee pad assembly according to claim 1, wherein said foam layer is selected from the group consisting of closed-cell ethylene vinyl acetate and polyurethane.

6. A knee pad assembly according to claim 1, wherein said flexible cover encloses the foam layer and the substrate, foam layer and cover are joined together to form a unitary structure for being molded while flexible to an aspect of the lower leg.

7. A knee pad assembly according to claim 6, wherein said cover is formed of a polyester sheeting fabric.

8. A knee pad assembly according to claim 7, wherein the length of the pad is at least twice as great as the width of the pad.

9. A knee pad assembly according to claim 1, wherein said reactive system comprises a blended polyisocyanate, polyol, catalyst and stabilizer.

10. A knee pad assembly according to claim 1, and including a first fastener attached to the upper surface for cooperating with a complementary second fastener attached to the strap for holding the pad in a fixed position along the strap while being worn.

11. A knee pad assembly according to claim 10, wherein one of said first and second fasteners comprises a patch of looped material, and the other of the first and second fasteners comprises a complementary patch of hooked material.

12. A knee pad assembly according to claim 1, wherein the first end of the strap includes a fastening ring connected thereto and adapted for receiving said second end therethrough for securing the strap around the lower leg.

13. A knee pad assembly according to claim 12, and including a third fastener attached to the second end of the strap for being releasably connected to said outer surface, thereby permitting the strap to be secured around the lower leg.

14. A knee pad assembly according to claim 13, wherein the outer surface of the strap comprises hook-and-loop material.

15. A knee pad assembly according to claim 14, wherein said third fastener comprises a patch of hook-and-loop material complementary to the outer surface.

16. A knee pad assembly product for relieving the symptoms of patellar tendinitis, comprising:
(a) an outer pouch formed of a moisture-impervious material;
(b) a pad having an upper surface positioned in said pouch in substantially moisture-free conditions and sealed therein against entry of moisture until use, and adapted for being positioned against and molded onto a lower leg in the region of the knee for lying in closely-conforming relation against and applying radially-directed pressure to the attachment site of the patellar tendon to the patellar, to the knee joint and to at least one epicondyle of the tibia and hardened into a rigid structure for therapeutic use, said pad comprising:
(i) an initially flexible substrate impregnated or coated with a reactive system, said system remaining stable when maintained in substantially moisture-free conditions and hardening upon exposure to moisture to form a rigid, self-supporting structure having a shape conforming to the lower leg to which the pad is molded during curing:
(ii) an inner foam layer overlying at least one side of the substrate;
(iii) a flexible outer layer enclosing said substrate and inner foam layer; and
(iv) a loop comprising a strip having first and second ends which are attached to said upper surface: and
(c) an elongate strap having an outer surface and first and second ends, said strap being disposed through said loop whereby said loop retains said strap against said upper surface of said pad so that the strap may extend around the lower leg for securing the pad in the closely conforming configuration against the lower leg.

17. A knee pad assembly product according to claim 16, wherein said outer moisture-proof pouch is formed of a laminated structure having at least one layer of plastic film and at least one layer of aluminum foil bonded to said plastic film.

18. A knee pad assembly product according to claim 16, wherein said substrate comprises a plurality of overlaid thicknesses of fiberglass.

19. A knee pad assembly product according to claim 18, wherein said plurality of thicknesses comprises at least three and no more than five thicknesses.

20. A knee pad assembly product according to claim 18, wherein said inner foam layer encloses the substrate therein.

21. A knee pad assembly product according to claim 18, wherein said foam layer is selected from the group consisting of closed-cell ethylene vinyl acetate and polyurethane.

22. A knee pad assembly product according to claim 16 wherein the substrate, foam layer and cover are joined together to form a unitary structure for being molded while flexible to an aspect of the lower leg and knee.

23. A knee pad assembly product according to claim 22, wherein said cover is formed of a polyester sheeting fabric.

24. A knee pad assembly product according to claim 16, wherein said reactive system comprises a blended polyisocyanate, polyol, catalyst and stabilizer.

25. A knee pad product according to claim 19, and including a first fastener attached to the upper surface for cooperating with a complementary second fastener attached to the strap for holding the pad in a fixed position along the strap while being worn.

26. A knee pad assembly product according to claim 25, wherein one of said first and second fasteners comprises a first patch of looped material, and the other of the first and second fasteners comprises a complementary second patch of hooked material.

27. A knee pad assembly product according to claim 26, wherein the first end of the strap includes a fastening ring connected thereto and adapted for receiving said second end therethrough for securing the strap around the lower leg.

28. A knee pad assembly product according to claim 26, and including a third fastener attached to the second end of the strap for being releasably connected to said outer surface, thereby permitting the strap to be secured around the lower leg.

29. A knee pad assembly product according to claim 28, wherein the outer surface of the strap comprises hook-and-loop material.

30. A knee pad assembly product according to claim 29, wherein said third fastener comprises a patch of hook-and loop material complementary to the outer surface.

* * * * *

UNITED STATES PATENT AND TRADEMARK OFFICE
CERTIFICATE OF CORRECTION

PATENT NO.    : 6,641,549 B2
DATED         : November 4, 2003
INVENTOR(S)   : Thomas D. Darcey

It is certified that error appears in the above-identified patent and that said Letters Patent is hereby corrected as shown below:

<u>Column 8,</u>
Line 60, before "(iii)" delete "and".
Line 67, delete first appearance of "loop restrains said".

<u>Column 9,</u>
Line 63, change ""patellar" to -- patella --.

Signed and Sealed this

Thirteenth Day of April, 2004

JON W. DUDAS
*Acting Director of the United States Patent and Trademark Office*